United States Patent [19]
Doi et al.

[11] Patent Number: 5,994,405
[45] Date of Patent: Nov. 30, 1999

[54] AGENT FOR CONTACT LENSES

[75] Inventors: Koji Doi; Shuuichi Nishihata; Takuya Nakajima, all of Kobe, Japan

[73] Assignee: Senju Pharmaceutical Co., Ltd., Osaka, Japan

[21] Appl. No.: 09/010,798

[22] Filed: Jan. 22, 1998

[30] Foreign Application Priority Data

Jan. 24, 1997 [JP] Japan ................................. 9-011699

[51] Int. Cl.$^6$ ................................................. A61K 31/16
[52] U.S. Cl. ............................................ 514/613; 514/912
[58] Field of Search ..................................... 514/613, 912

[56] References Cited

PUBLICATIONS

WPID 67–09802G (1993).

Primary Examiner—Zohreh Fay
Attorney, Agent, or Firm—Wenderoth, Lind & Ponack, L.L.P.

[57] ABSTRACT

An agent for contact lenses, comprising chloroacetamide. According to the present invention, chloroacetamide, which is the bacteriocidal component to be contained, is scarcely adsorbed not only to hard contact lenses and gas-permeable hard contact lenses, but also to soft contact lenses, and even if adsorbed, moreover, chloroacetamide is quickly released and is not accumulated on the contact lens to a greater extent. The inventive agent containing, in addition to chloroacetamide, sodium lauryl sulfate shows more superior bacteriocidal effect and cleaning effect. Therefore, the present invention provides an agent for contact lenses having superior bacteriocidal effect and cleaning effect, which can be used safely and with ease for various contact lenses inclusive of soft contact lenses.

13 Claims, No Drawings

AGENT FOR CONTACT LENSES

TECHNICAL FIELD OF THE INVENTION

The present invention relates to an agent for contact lenses having superior bacteriocidal action, which can be used for hard contact lenses, gas-permeable hard contact lenses and soft contact lenses, wherein its bacteriocidal component is less adsorbed to contact lenses and, even if adsorbed, can be released quickly and accumulated less.

BACKGROUND OF THE INVENTION

Various contact lenses such as hard contact lens, gas-permeable hard contact lens, soft contact lens and the like have been rapidly prevailing in recent years. These contact lenses are sterilized by a bacteriocidal method including boiling or immersion in an agent for contact lenses containing a bacteriocidal agent. Sterilization by boiling shows superior effect, but requires complicated steps and may cause degradation of the contact lens.

While a method using a bacteriocidal agent can be conducted rather easily, the bacteriocidal agent widely used conventionally, such as benzalkonium chloride, benzethonium chloride, p-hydroxybenzoate, chlorohexydine gluconate, cetylpyridinium chloride and the like, are known to be readily adsorbed particularly onto soft contact lenses, and once adsorbed, are hardly released but accumulated on the lenses. When, for example, a contact lens, to which such bacteriocidal agent has been adsorbed and accumulated thereon, is worn, the anterior ocular segment tissue is stimulated and may develop allergic reaction, inflammation, corneal erosion and the like.

Therefore, an agent for contact lenses capable of superior bacteriocidal performance has been awaited, which is associated with less adsorption of the bacteriocidal agent contained therein onto any contact lenses and quick release thereof even if adsorbed, thus being less accumulative, and which can be used safely for any contact lenses with easy operation.

SUMMARY OF THE INVENTION

An object of the present invention is to provide an agent for contact lenses having superior bacteriocidal action, which shows less adsorption of bacteriocidal component onto any contact lenses inclusive of soft contact lenses, and quick release thereof even if adsorbed, thus being less accumulative.

As a result of the study and investigation in an attempt to solve the above-mentioned problems, the present inventors have found that chloroacetamide, which is one of the bacteriocidal agents, is adsorbed extremely less to hard contact lenses and gas-permeable hard contact lenses, as well as to soft contact lenses, and that even if adsorbed, it can be released extremely easily with least accumulation on the contact lenses.

The present inventors have further found that the concurrent use of chloroacetamide and sodium lauryl sulfate in an agent for contact lenses leads to the exertion of most superior bacteriocidal effect and cleaning effect by said agent.

Accordingly, the present invention provides the following.

(1) An agent for contact lenses, containing chloroacetamide.
(2) The agent of (1) above, further containing at least one member selected from the group consisting of a buffer, an isotonizing agent, a surfactant, a chelating agent, a thickener, a wetting agent and a cleaning capacity enhancer.
(3) The agent of (1) above, containing chloroacetamide in a concentration of 0.001–10 (W/V)%.
(4) The agent of (2) above, containing chloroacetamide in a concentration of 0.001–10 (W/V)%.
(5) The agent of (1) above, further containing sodium lauryl sulfate.
(6) The agent of (2) above, further containing sodium lauryl sulfate.
(7) The agent of (3) above, further containing sodium lauryl sulfate.
(8) The agent of (4) above, further containing sodium lauryl sulfate.
(9) The agent of (5) above, containing sodium lauryl sulfate in a concentration of 0.00001–1.0 (W/V)%.
(10) The agent of (6) above, containing sodium lauryl sulfate in a concentration of 0.00001–1.0 (W/V)%.
(11) The agent of (7) above, containing sodium lauryl sulfate in a concentration of 0.00001–1.0 (W/V)%.
(12) The agent of (8) above, containing sodium lauryl sulfate in a concentration of 0.00001–1.0 (W/V)%.

DETAILED DESCRIPTION OF THE INVENTION

While chloroacetamide has been known as an antiseptic for cosmetics and the like, the present inventors are not aware of an agent for contact lenses containing the same.

The inventive agent for contact lenses contains chloroacetamide in a concentration of 0.001–10 (W/V)%, preferably 0.05–5 (W/V)%, when in use.

Sodium lauryl sulfate is also known as a surfactant etc., whereas the use thereof together with chloroacetamide for an agent for contact lenses has not been known.

The inventive agent for contact lenses contains sodium lauryl sulfate in a concentration of 0.00001–1.0 (W/V)%, preferably 0.001–0.01 (W/V)%, when in use.

The inventive agent for contact lenses can be used, for example, as a bacteriocidal agent, a preservative, a cleaning agent and the like for contact lenses. It can be applied to various uses as an agent for contact lenses, and may be used as a bacteriocidal agent and preservative, or a bacteriocidal agent, preservative and cleaning agent contained in one solution.

The inventive agent for contact lenses can contain other bacteriocidal agent, a buffer, an isotonizing agent, a surfactant, a chelating agent, a thickener, a wetting agent, a cleaning capability enhancer and the like, as long as the object of the present invention is not impaired.

The bacteriocidal agent to be used depends on the type of each contact lens: hard contact lens, gas-permeable hard contact lens or soft contact lens. However, as long as the object of the present invention is not adversely affected, for example, benzethonium chloride, chlorohexydine gluconate, sorbic acid and salt thereof, thimerosal, chlorobutanol, phenethyl alcohol, p-hydroxybenzoates and the like may be also used.

The buffer is used at a concentration which makes the pH of the inventive agent for contact lenses about 4 to 10, preferably 5 to 8. Examples of the buffer include combinations of an acid and a salt thereof or a base and a salt thereof according to a conventional method to make the pH a desirable one. For example, combinations of boric acid, sodium borate, citric acid, sodium citrate, tartaric acid, sodium tartrate, gluconic acid, sodium gluconate, acetic acid, sodium acetate, phosphoric acid, disodium hydrogen phosphate, sodium dihydrogen phosphate, various amino acids and the like are used.

The isotonizing agent is subject to no particular limitation as long as it is water soluble and does not show adverse influence such as irritation to the eye. Examples thereof include sodium chloride, potassium chloride, calcium chloride, glycerol and the like.

The surfactant may be non-ionic, anionic, amphoteric or cationic. The surfactant is used as a bacteriocidal agent, cleaning capability enhancer and the like.

Examples of anionic surfactant include sodium lauroyl sarcosinate, triethanolamine lauroyl-L-glutamate, sodium myristyl sarcosinate and the like. Examples of amphoteric surfactant include lauryl dimethylamino-acetic betaine, 2-alkyl-N-carboxymethyl-N-hydroxyethylimidazolinium betaine, hydrochloric alkyldiaminoglycine and the like. Examples of non-ionic surfactant include polysorbate 80, polyoxyethylene hydrogenated castor oil 60, polyoxyl 40 stearate, polyoxyethylene lauryl ether and the like, and examples of cationic surfactant include benzethonium chloride, benzalkonium chloride, cetylpyridinium chloride and the like.

The chelating agent is exemplified by sodium edetate, sodium citrate, condensed sodium phosphate and the like.

The thickener is exemplified by hydroxyethylcellulose, methylcellulose, polyvinyl alcohol, polyvinylpyrrolidone and the like.

The wetting agent is exemplified by glycerol, polyethylene glycol, propylene glycol and the like.

The cleaning capability enhancer is exemplified by proteolytic enzyme, lipolytic enzyme, polysaccharide-degrading enzyme, peroxide, surfactant and the like. Examples of the proteolytic enzyme include papain, pancreatin, trypsin, bromelain and the like. Examples of the lipolytic enzyme include phospholipase, pancreatic lipase and the like. The polysaccharide-degrading enzyme is exemplified by chitosan-degrading enzyme, mucin-degrading enzyme, lysozyme, heparinase, hyaluronidase and the like. Peroxide may be, for example, percarbonate, perborate, hydrogen peroxide and the like. The surfactant is exemplified by those mentioned above.

The form of the agent for contact lenses of the present invention is subject to no particular limitation as long as it can be prepared into a liquid when in use. Examples thereof include a liquid agent and a solid agent which is preserved for a long time and dissolved when in use. Examples of the solid agent include tablets, granules, powders and lyophilized products. In view of the quick dissolution and sterilization, uniform composition and the like, lyophilized products are preferable. They can be produced by a conventional method.

Note that the content and pH of the above-mentioned chloroacetamide, sodium lauryl sulfate and other components in a solid agent are such that they would make the content and pH of a liquid agent thereof the above-mentioned values.

The agent for the contact lenses of the present invention is used as a bacteriocidal agent for contact lenses, for example, by immersing a contact lens after use in this bacteriocidal solution and keeping same therein for 1 to 12 hours. It does not require a special boiling.

The inventive agent for contact lenses containing, in addition to chloroacetamide, sodium lauryl sulfate, shows more superior bacteriocidal and cleaning capabilities. In particular, one containing a cleaning capacity enhancer shows more effective cleaning effect. The agent for contact lenses of the present invention is hardly adsorbed to soft contact lenses, and particularly useful as an agent for soft contact lenses.

The present invention is described in more detail by way of Examples, which should not be construed as limiting the invention.

EXAMPLE 1

EXPERIMENTAL EXAMPLE 1

An aqueous solution of chloroacetamide (0.1 W/V%) was precisely taken by 1 ml in a vial. One soft contact lens, the dry weight of which had been measured, was immersed in said aqueous solution. The solution with the lens was shaken at room temperature for 24 hr, where a solution without a lens was used as a control, and a decrease in chloroacetamide was taken as an amount taken into the soft contact lens. The chloroacetamide content was determined by high performance liquid chromatography.

(Soft contact lens used)

soft contact lens (No. 1)
main material: poly(hydroxyethyl methacrylate)
water content: low (about 35%)

soft contact lens (No. 2)
main material: poly(methyl methacrylate)+ polyvinylpyrrolidone
water content: high (about 77%)

(Results and discussion)

The results were as follows.

Residual chloroacetamide in the test solution where soft contact lens (No. 1) was immersed: 97%

Residual chloroacetamide in the test solution where soft contact lens (No. 2) was immersed: 96%

The results reveal that chloroacetamide was taken into the both lenses by only 3–4%, which was very small.

EXPERIMENTAL EXAMPLE 2

In the same manner as in Experimental Example 1, a soft contact lens was immersed in an aqueous solution of chloroacetamide (0.1 W/V%) for 24 hr and gently dried. The wet weight was measured and the lens was placed in a vial where physiological saline (1 mL) was precisely taken. The vial was shaken at room temperature for 2 hr. The soft contact lens was taken out and dried gently. The lens was placed in a new vial containing physiological saline (1 mL) and shaken for 3 hr. The total of the chloroacetamide content in the test solutions in both vials was taken as the amount of release from the soft contact lens.

The results were as follows. The percent release of chloroacetamide was about 100% in 5 hr, which release rate was quick.

Percent release of chloroacetamide from soft contact lens (No. 1): 100%

Percent release of chloroacetamide from soft contact lens (No. 2): 100%

EXAMPLE 2

The agent for contact lenses of the present invention having the following formulation was prepared.

| | |
|---|---|
| chloroacetamide | 0.1 g |
| sodium lauryl sulfate | 1 g |
| boric acid | 1 g |
| sodium borate | 1 g |
| EDTA | 0.5 g |

EXAMPLE 3

The agent for contact lenses of the present invention having the following formulation was prepared.

| | |
|---|---|
| chloroacetamide | 1 g |
| sodium lauryl sulfate | 0.1 g |
| boric acid | 1 g |
| sodium borate | 1 g |
| EDTA | 0.5 g |
| sorbic acid | 0.05 g |
| sterile distilled water | appropriate amount |
| total | 100 ml |

EXAMPLE 4

The agent for contact lenses of the present invention having the following formulation was prepared.

| | |
|---|---|
| chloroacetamide | 1 g |
| sodium lauryl sulfate | 0.05 g |
| boric acid | 1 g |
| sodium borate | 1 g |
| EDTA | 0.5 g |
| sorbic acid | 0.05 g |
| sterile distilled water | appropriate amount |
| total | 100 ml |

EXPERIMENTAL EXAMPLE 3

Bacteriocidal effect of the agent for contact lenses of the present invention
(1) test bacteria

*Staphylococcus aureus* IFO 13276

*Escherichia coli* IFO 3972

*Pseudomonas aeruginosa* IFO 13275

(2) test method

The agents for contact lenses of Examples 2, 3 and 4 were used as test solutions. The above-mentioned test bacteria were inoculated to each test solution at a concentration of $10^3$ CFU/mL, and the bacteria were stood at room temperature for 4 hr. Then, 0.5 mL each of the test solution was added to 4.5 mL of physiological saline, and 1 mL thereof was transferred to a dish, to which an SCDLP agar medium was added and incubated at 37° C. for 48 hr. The number of viable cells was counted from the colonies formed. The results are shown in Table 1.

The test solutions A to C having the following formulations were prepared and subjected to the same steps as above, and the number of viable cells was counted from the colonies formed. The results are shown in Table 1.

| (Test solution A) | |
|---|---|
| chloroacetamide | 1 g |
| sodium lauryl sulfate | 0.1 g |
| sterile distilled water | appropriate amount |
| total | 100 ml |

| (Test solution B) | |
|---|---|
| chloroacetamide | 1 g |
| sodium lauryl sulfate | 0.05 g |
| sterile distilled water | appropriate amount |
| total | 100 ml |

| (Test solution C) | |
|---|---|
| sodium lauryl sulfate | 0.1 g |
| sterile distilled water | appropriate amount |
| total | 100 ml |

TABLE 1

| | | viable cell counts of test bacteria (log CFU/mL) | | |
|---|---|---|---|---|
| Test solution | (on inoculation) | S 3 | E 3 | P 3 |
| Agent of Example 2 | | 0 | 0 | 0 |
| Agent of Example 3 | | 0 | 0 | 0 |
| Agent of Example 4 | | 0 | 0 | 0 |
| Test solution A | | 0 | 0 | 0 |
| Test solution B | | 0 | 0 | 0 |
| Test solution C | | 0 | 3 | 1 |

S: *Staphylococcus aureus* IFO 13276
E: *Escherichia coli* IFO 3972
P: *Pseudomonas aeruginosa* IFO 13275

The foregoing results show that the addition of both chloroacetamide and sodium lauryl sulfate to an agent for contact lenses leads to the exertion of more superior bacteriocidal effect.

According to the agent for contact lenses of the present invention, chloroacetamide, which is the bacteriocidal component to be contained, is scarcely adsorbed not only to hard contact lenses and gas-permeable hard contact lenses, but also to soft contact lenses, and when a soft contact lens is immersed in said agent for a long time, chloroacetamide is adsorbed to the contact lens only at an extremely low level. Even if adsorbed, moreover, chloroacetamide is quickly released and is not accumulated on the contact lens to a greater extent. The inventive agent containing, in addition to chloroacetamide, sodium lauryl sulfate shows more superior bacteriocidal effect and cleaning effect. Therefore, the present invention provides an agent for contact lenses having superior bacteriocidal effect and cleaning effect, which can be used safely and with ease for various contact lenses inclusive of soft contact lenses.

This application is based on application Ser. No. 11699/1997 filed in Japan, the content of which is incorporated hereinto by reference.

What is claimed is:

1. A composition for contact lenses, comprising chloroacetamide and sodium lauryl sulfate.

2. The composition of claim 1, further comprising at least one member selected from the group consisting of a buffer, an isotonizing agent, a surfactant, a chelating agent, a thickener, a wetting agent and a cleaning capacity enhancer.

3. The composition of claim 1, comprising chloroacetamide in a concentration of 0.001–10 (W/V)%.

4. The composition of claim 2, comprising chloroacetamide in a concentration of 0.001–10 (W/V)%.

5. The composition of claim 1, comprising sodium lauryl sulfate in a concentration of 0.00001–1.0 (W/V)%.

6. The composition of claim 2, comprising sodium lauryl sulfate in a concentration of 0.00001–1.0 (W/V)%.

7. The composition of claim 3, comprising sodium lauryl sulfate in a concentration of 0.00001–1.0 (W/V)%.

8. The composition of claim 4, comprising sodium lauryl sulfate in a concentration of 0.00001–1.0 (W/V)%.

9. A method for disinfecting contact lenses, which comprises:

contacting contact lenses with a composition comprising chloroacetamide.

10. The method according to claim 9, wherein the composition further comprises at least one member selected from the group consisting of a buffer, an isotonizing agent, a surfactant, a chelating agent, a thickener, a wetting agent and a cleaning capacity enhancer.

11. The method according to claim 9, wherein the chloroacetamide in the composition is present in a concentration of 0.001–10 (W/V)%.

12. The method according to claim 9, wherein the composition further comprises sodium lauryl sulfate.

13. The method according to claim 12, wherein the sodium lauryl sulfate is present in a concentration of 0.00001–1.0 (W/V)%.

* * * * *